United States Patent [19]
Park et al.

[11] Patent Number: 5,242,944
[45] Date of Patent: Sep. 7, 1993

[54] PHENYLACETAMIDE DERIVATIVES AND PHARMACEUTICAL COMPOSITIONS THEREOF

[75] Inventors: No S. Park; Deok C. Ha; Joong K. Choi; Hyun S. Kim; Mi S. Hong, all of Daejeon; Hee J. Lim, Pusan; Kwang S. Lee, Cheonan, all of Rep. of Korea

[73] Assignee: Korea Research Institute of Chemical Technology, Daejeon, Rep. of Korea

[21] Appl. No.: 868,033

[22] Filed: Apr. 13, 1992

Related U.S. Application Data

[63] Continuation-in-part of Ser. No. 718,007, Jun. 20, 1991, abandoned.

[30] Foreign Application Priority Data

| | | |
|---|---|---|
| Jul. 30, 1991 [KR] | Rep. of Korea | 91-13094 |
| Jul. 30, 1991 [KR] | Rep. of Korea | 91-13095 |
| Jul. 30, 1991 [KR] | Rep. of Korea | 91-13096 |
| Nov. 6, 1991 [KR] | Rep. of Korea | 91-19641 |

[51] Int. Cl.$^5$ .................. A61K 31/165; C07C 233/04
[52] U.S. Cl. .................... 514/466; 514/620; 549/441; 564/165
[58] Field of Search .................. 564/165; 549/441; 514/466, 620

[56] References Cited

U.S. PATENT DOCUMENTS

| | | | |
|---|---|---|---|
| 4,313,958 | 2/1982 | LeHann | 424/324 |
| 4,424,205 | 1/1984 | LaHann et al. | 424/72 |
| 5,045,565 | 9/1991 | Gardner et al. | 514/487 |

FOREIGN PATENT DOCUMENTS

0282127A2  9/1988  European Pat. Off. .
2168975A   7/1986  United Kingdom .

OTHER PUBLICATIONS

Yaksh et al., Science 206, 1979, pp. 481–483.
Makovec et al., Chemical Abstracts, vol. 83 (1975) 193728p.

Primary Examiner—Richard L. Raymond
Attorney, Agent, or Firm—Michael N. Meller

[57] ABSTRACT

The present invention provides novel phenylacetamide derivatives having the following formula

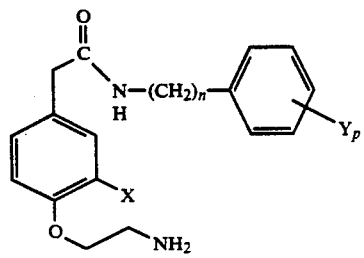

wherein:

X is a hydrogen, halogen, hydroxy, nitro, amino, $R^1$, $NR^1R^2$, $NHR^1$ or $OR^1$ wherein $R^1$ and $R^2$ are an optionally substituted $C_{1-8}$ alkyl, cycloalkyl or benzyl group, respectively; Y, which may be the same or different when p is greater than 1, is a hydrogen, halogen, methylenedioxy, hydroxy, trifluoromethyl, $R^3$ or $OR^3$ wherein $R^3$ is an optionally substituted $C_{1-8}$ alkyl or benzyl group;

n is an integer from 1 to 6; and p is an integer from 1 to 5; and pharmaceutically acceptable salts thereof which have powerful analgesic and anti-inflammatory activities.

The invention also provides processes for preparing these compounds and pharmaceutical compositions containing them as an active ingredient.

15 Claims, No Drawings

PHENYLACETAMIDE DERIVATIVES AND PHARMACEUTICAL COMPOSITIONS THEREOF

REFERENCE TO RELATED APPLICATION

This application is a continuation-in-part of U.S. Ser. No. 718,007 which was filed on Jun. 20, 1991, now abandoned.

FIELD OF THE INVENTION

The present invention relates to novel phenylacetamide derivatives; and, more specifically, relates to phenylacetamide derivatives which have powerful anti-inflammatory and analgesic activities, pharmaceutically acceptable salts thereof and processes for the preparation thereof.

BACKGROUND OF THE INVENTION

Hitherto, it has been known that capsaicin of the following formula(A)

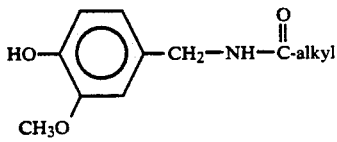

which may be extracted from the fruit of a plant belonging to the genus Cayenne has an analgesic property. Such natural capsaicin(i.e., trans-8-methyl-N-vanillyl-6-nonenamide) and a synthetic capsaicin (N-vanillyl-nonanamide) have been described in U.S. Pat. No. 4,313,958 as an analgesic. Also, similar results of chemical and pharmacological studies have been reported in various references [see, e.g., Yaksh, et al., Science, 206, pp 481–483(1979); and The Alkaloids, Vol. XXIII, pp 227–299(1984), Academic Press].

Described in EP Publication No. 0,282,127 as having anti-inflammatory or analgesic activity are the aminoethoxybenzylamine derivatives of the following formula(B)

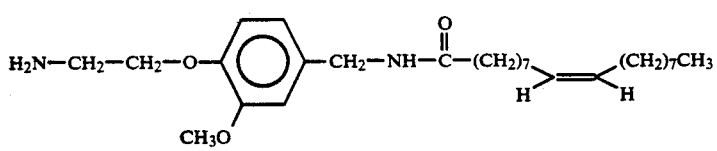

Further, U.S. Pat. No. 4,424,205(EP Publication No. 0,089,710) filed by T. R. LaHann et al. discloses the analgesic and/or anti-irritant compounds of the following formula(C)

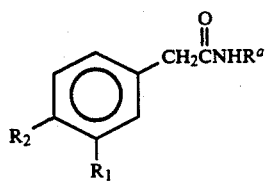

wherein $R^a$ is a linear or branched $C_3$–$C_{11}$ alkyl, alkynyl or aralkyl group, a linear or branched $C_3$–$C_{22}$ alkenyl group, or an unbranched or branched $C_6$–$C_{11}$ cycloalkyl or cycloalkenyl group; and one of $R_1$ and $R_2$ is OH, the other being OH or H.

U. K. Patent Publication No. 2,168,975 filed by J. M. Janusz also provides aralkanamides having formula(D)

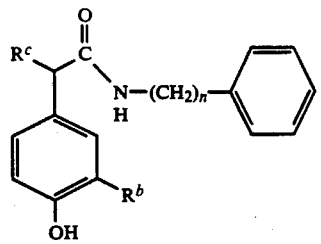

wherein $R^b$ represents H, OH, $OCH_3$ or $OCH_2CH_3$; $R^c$ represents H or $CH_3$; and n is an integer from 0 to 12.

Gardner et al. generically discloses in U.S. Pat. No. 5,045,565 β-aminoethyl-substituted phenyl compounds, including a compound of formula(E):

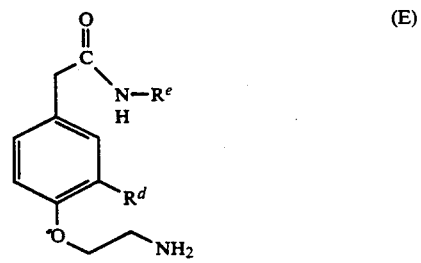

wherein,
$R^d$ is a hydrogen, or a hydroxy or methoxy group; and
$R^e$ is a $C_{1-24}$ alkyl group.

According to the detailed description of the Gardner patent the term "alkyl" is defined to include straight carbon chains optionally substituted with aryl, which is, in turn, defined to include a phenyl optionally substituted with a halogen, hydroxy, $C_1$–$C_{16}$ alkoxy, amino, nitro, cyano, phenyl, benzyl, benzyloxy, trifluoromethyl, formylamino, carboxylate or $C_1$–$C_6$ alkyl group.

Although the Gardner patent discloses alkyl substituted phenyl acetamide derivatives of the above formula(E), it fails to, e.g., describe N-n-alkyl substituted phenyl acetamides with a phenyl group attached to the end of the n-alkyl group.

The foregoing prior art capsaicin derivatives can be characterized by their having a saturated or unsaturated alkyl group of 3 to 24 carbon atoms or an unsubstituted ω-phenyl alkyl group attached to the carbonyl group. These compounds are, however, generally known to have several side-effects: for example, strong irritation, reddening of skin and toxicity.

SUMMARY OF THE INVENTION

To ameliorate the afore-mentioned problems, therefore, the present inventors have successfully worked toward the development of novel phenylacetamide derivatives which have powerful analgesic and anti-inflammatory activities with little or much reduced level of irritation and toxicity. Specifically, the invention provides novel phenylacetamide derivatives of the following formula(I)

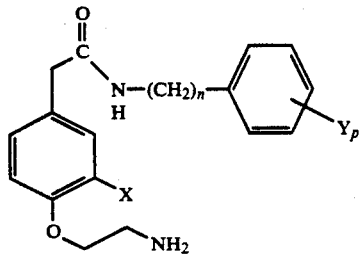

wherein:

X is a hydrogen, halogen, hydroxy, nitro, amino, $R^1$, $NR^1R^2$, $NHR^1$ or $OR^1$ wherein $R^1$ and $R^2$ are an optionally substituted $C_{1-8}$ alkyl, cycloalkyl or benzyl group, respectively;

Y, which may be the same or different when p is greater than 1, is a hydrogen, halogen, methylenedioxy, hydroxy, trifluoromethyl, $R^3$ or $OR^3$ wherein $R^3$ is an optionally substituted $C_{1-8}$ alkyl or benzyl group;

n is an integer from 1 to 6; and p is an integer from 1 to 5.

In the context of the present invention and specification, unless otherwise specifically mentioned, the term "phenylacetamide derivatives" shall be taken to include pharmaceutically acceptable salts thereof.

In another aspect, the present invention provides processes for the preparation of these compounds and medicinal formulations containing them as an active ingredient.

DETAILED DESCRIPTION OF THE INVENTION

Preferred compounds of the present invention include the compounds of formula(I) wherein X is a hydrogen, halogen, hydroxy, nitro, amino or $OR^1$; Y, which may be identical or different when p is greater than 1, is a hydrogen, halogen, trifluoromethyl or $R^3$; n is an integer from 2 to 5; p is an integer from 1 to 3; and $R^1$ and $R^3$ have the same meanings as defined above.

More preferred compounds of the present invention are the compounds of formula(I) wherein X is a halogen, hydroxy, nitro, amino or $OR^1$; Y, which may be identical or different when p is 2, is a hydrogen, halogen, trifluoromethyl or $R^3$; n is 3 or 4; p is 1 or 2; and $R^1$ and $R^3$ are an optionally substituted $C_{1-5}$ alkyl, respectively.

Pharmaceutically acceptable salts of the compounds having the formula(I) according to the present invention may be the salts of inorganic acids such as hydrochloric acid, hydrogen bromide, sodium hydrogen sulfate and carbonic acid, or of organic acids such as formic, acetic, oxalic, benzoic, citric, tartaric, gluconic, gentisic, fumaric and lactobionic acids.

The present invention also includes within its scope pharmaceutical compositions comprising one or more of the phenylacetamide derivatives of formula(I) as active ingredients, in association with a possible pharmaceutically acceptable carrier. The term "(pharmaceutical) carrier", as used herein, means one or more compatible solid or liquid filler, diluents or encapsulating materials which are suitable for a human or animal administration. The compatible carriers, as used herein, are the components that do not cause any interactions which substantially reduce the efficacy of the pharmaceutical composition in an ordinary user environment. Possible pharmaceutical carriers must be of sufficiently low toxicity to make them suitable for administration to the subject of treatment.

Some examples of substances which can serve as the carrier are sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline phosphate buffer solutions, cocoa buffer(suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, tabletting agents, stabilizers, antioxidants and preservatives may also be present. Other compatible additives and ingredients such as pain killers, muscle relaxants may be included in the possible pharmaceutical carrier for use in the compositions of the present invention.

The proper pharmaceutical carriers of the present invention are basically determined by the administration route. The compounds of the present invention may be administered by injection, orally and topically. If the compound is to be injected, the preferred carrier is the sterile, physiological saline with pH 4. If the compound is to be applied topically, the carrier may preferably comprise those suited for use in creams, gels, tapes and the like. And the pharmaceutical carriers for oral administration may include those suited for tablets and capsules.

The carrier may comprise, in total, from about 0.1% to about 99.99999% by weight of the pharmaceutical compositions of the present invention, mainly from about 50% to about 99.9999%.

Total single dosages of the compounds of the present invention are generally from about 1 μg to about 10 g. Preferred single dosages are from about 1 μg to about 3500 mg; and more preferred are from about 1 μg to 1000 mg; and most preferred are from about 1 μg to about 600 mg.

Possible pharmaceutical carriers suitable for the preparation of unit dosage forms for oral administration and injection, and dosage forms for topical application are well-known in the art. Their selection may further depend on secondary considerations such as taste, cost, and/or shelf stability, which are not critical for the purposes of the present invention; and may be made without difficulty by a person skilled in the art.

The phenylacetamide derivatives having the formula(I) according to the present invention may be prepared in accordance with the procedure comprising the steps of: (i) reacting an amine compound of the formula(II) with a para-hydroxyphenylacetic acid of the formula(III) to provide a compound of the formula(IV); (ii) reacting the compound(IV) with 1,2-dibromoethane to provide a compound of the formula(V); (iii) reacting the compound(V) with sodium azide(NaN₃) to provide a compound of the formula(VI); and then (iv) converting the compound(VI) to the compound of the formula(I), as further described below:

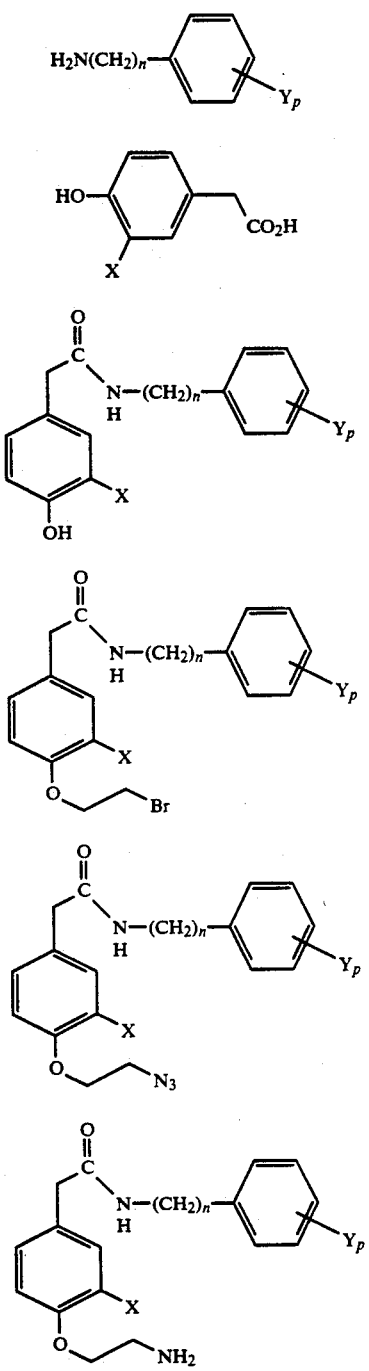

In the above process, step(i) may be conducted by heating the reactants at a temperature ranging from 130° C. to 160° C. for 2 to 5 hours in the presence of a catalyst such as 3 Å, 4 Å or 5 Å, and preferably 4 Å, powdered molecular sieve without any solvent.

Step(ii) may be conducted in the presence of a base such as sodium hydride(NaH) in a solvent, e.g., tetrahydrofuran, at the boiling point of the solvent.

Step(iii) of the process may be carried out in the presence of a catalyst such as n-tetrabutyl ammonium bromide(n-Bu$_4$NBr) in a solvent, e.g., benzene, at the boiling temperature of the solvent.

Finally, step(iv) may be carried out by reducing the product from step(iii) in the presence of palladium-on-carbon(Pd-C) as a catalyst under an elevated hydrogen pressure or by reacting the product of step(iii) with triphenylphosphine in the presence of water and the tetrahydrofuran solvent to obtain the compound of the formula(I) wherein X is nitro.

In step(i) above, the compound of the formula(IV) is obtained as an intermediate for preparing the final compound of the present invention; and it is found that the intermediate itself also has analgesic and anti-inflammatory effects.

An amine compound of the formula(II) used in preparing the compounds of the present invention as a starting material may be obtained from the compound of the formulae(VII) or from the compound of the formula(VIII)

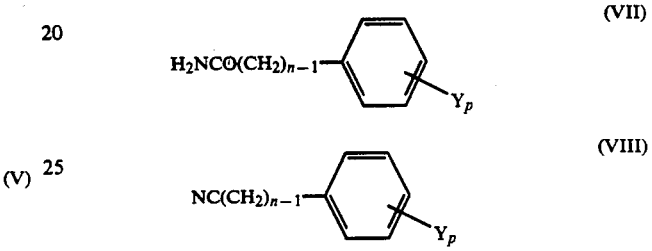

wherein Y, n and p have the same meanings as previously defined, by employing a conventional method such as a reduction method using an alanate, e.g., lithium aluminium hydride(LiAlH$_4$), etc., or a hydrogenation method using a metal such as palladium, Raney nickel as a catalyst. An acid compound of formula(III) is commercially available and also can be prepared using a partial protection method.

Specifically, representative examples of the phenyl acetamide derivatives having formula(I) of the present invention are as follows:

N-{3-(3,4-dimethylphenyl)propyl}-4-(2-aminoethoxy)-3-hydroxyphenylacetamide;

N-{2-(3,4-dimethylphenyl)ethyl}-4-(2-aminoethoxy)-3-hydroxyphenylacetamide;

N-(3-phenylpropyl)-4-(2-aminoethoxy)-3-hydroxyphenylacetamide;

N-{3-(3-methylphenyl)propyl}-4-(2-aminoethoxy)-3-hydroxyphenylacetamide;

N-{3-(4-methylphenyl)propyl}-4-(2-aminoethoxy)-3-hydroxyphenylacetamide;

N-{3-(4-chlorophenyl)propyl}-4-(2-aminoethoxy)-3-hydroxyphenylacetamide;

N-{3-(3,4-dichlorophenyl)propyl}-4-(2-aminoethoxy)-3-hydroxyphenylacetamide;

N-{3-(4-fluorophenyl)propyl}-4-(2-aminoethoxy)-3-hydroxyphenylacetamide;

N-{3-(3,4-methylenedioxyphenyl)propyl}-4-(2-aminoethoxy)-3-hydroxyphenylacetamide;

N-{3-(3-methoxyphenyl)propyl}-4-(2-aminoethoxy)-3-hydroxyphenylacetamide;

N-{3-(3-trifluoromethylphenyl)propyl}-4-(2-aminoethoxy)-3-hydroxyphenylacetamide;

N-{3-(3,5-dimethylphenyl)propyl}-4-(2-aminoethoxy)-3-hydroxyphenylacetamide;

N-{3-(3-ethylphenyl)propyl}-4-(2-aminoethoxy)-3-hydroxyphenylacetamide;

N-(4-phenylbutyl)-4-(2-aminoethoxy)-3-hydroxyphenylacetamide;

N-{4-(3,4-dimethylphenyl)butyl}-4-(2-aminoethoxy)-3-hydroxyphenylacetamide;
N-(5-phenylpentyl)-4-(2-aminoethoxy)-3-hydroxyphenylacetamide;
N-{3-(3,4-dimethylphenyl)propyl}-4-(2-aminoethoxy)-3-nitrophenylacetamide;
N-{2-(3,4-dimethylphenyl)ethyl}-4-(2-aminoethoxy)-3-nitrophenylacetamide;
N-(3-phenylpropyl)-4-(2-aminoethoxy)-3-nitrophenylacetamide;
N-{3-(3-methylphenyl)propyl}-4-(2-aminoethoxy)-3-nitrophenylacetamide;
N-{3-(4-methylphenyl)propyl}-4-(2-aminoethoxy)-3-nitrophenylacetamide;
N-{3-(4-chlorophenyl)propyl}-4-(2-aminoethoxy)-3-nitrophenylacetamide;
N-{3-(3,4-dichlorophenyl)propyl}-4-(2-aminoethoxy)-3-nitrophenylacetamide;
N-{3-(4-fluorophenyl)propyl}-4-(2-aminoethoxy)-3-nitrophenylacetamide;
N-{3-(3,4-methylenedioxyphenyl)propyl}-4-(2-aminoethoxy)-3-nitrophenylacetamide;
N-{3-(3-methoxyphenyl)propyl}-4-(2-aminoethoxy)-3-nitrophenylacetamide;
N-{3-(3-trifluoromethylphenyl)propyl}-4-(2-aminoethoxy)-3-nitrophenylacetamide;
N-{3-(3,5-dimethylphenyl)propyl}-4-(2-aminoethoxy)-3-nitrophenylacetamide;
N-{3-(3-ethylphenyl)propyl}-4-(2-aminoethoxy)-3-nitrophenylacetamide;
N-(4-phenylbutyl)-4-(2-aminoethoxy)-3-nitrophenylacetamide;
N-{4-(3,4-dimethylphenyl)butyl}-4-(2-aminoethoxy)-3-nitrophenylacetamide;
N-(5-phenylpentyl)-4-(2-aminoethoxy)-3-nitrophenylacetamide;
N-{3-(3,4-dimethylphenyl)propyl}-4-(2-aminoethoxy)-3-aminophenylacetamide;
N-{2-(3,4-dimethylphenyl)ethyl}-4-(2-aminoethoxy)-3-aminophenylacetamide;
N-(3-phenylpropyl)-4-(2-aminoethoxy)-3-aminophenylacetamide;
N-{3-(3-methylphenyl)propyl}-4-(2-aminoethoxy)-3-aminophenylacetamide;
N-{3-(4-methylphenyl)propyl}-4-(2-aminoethoxy)-3-aminophenylacetamide;
N-{3-(4-chlorophenyl)propyl}-4-(2-aminoethoxy)-3-aminophenylacetamide;
N-{3-(3,4-dichlorophenyl)propyl}-4-(2-aminoethoxy)-3-aminophenylacetamide;
N-{3-(4-fluorophenyl)propyl}-4-(2-aminoethoxy)-3-aminophenylacetamide;
N-{3-(3,4-methylenedioxyphenyl)propyl}-4-(2-aminoethoxy)-3-aminophenylacetamide;
N-{3-(3-methoxyphenyl)propyl}-4-(2-aminoethoxy)-3-aminophenylacetamide;
N-{3-(3-trifluoromethylphenyl)propyl}-4-(2-aminoethoxy)-3-aminophenylacetamide;
N-{3-(3,5-dimethylphenyl)propyl}-4-(2-aminoethoxy)-3-aminophenylacetamide;
N-{3-(3-ethylphenyl)propyl}-4-(2-aminoethoxy)-3-aminophenylacetamide;
N-(4-phenylbutyl)-4-(2-aminoethoxy)-3-aminophenylacetamide;
N-{4-(3,4-dimethylphenyl)butyl}-4-(2-aminoethoxy)-3-aminophenylacetamide;
N-(5-phenylpentyl)-4-(2-aminoethoxy)-3-aminophenylacetamide;
N-{3-(4-chlorophenyl)propyl}-4-(2-aminoethoxy)-phenylacetamide;
N-{3-(4-chlorophenyl)propyl}-4-(2-aminoethoxy)-3-fluorophenylacetamide;
N-{3-(4-chlorophenyl)propyl}-4-(2-aminoethoxy)-3-chlorophenylacetamide;
N-{3-(4-chlorophenyl)propyl}-4-(2-aminoethoxy)-3-methoxyphenylacetamide;
N-{3-(2,4-dichlorophenyl)propyl}-4-(2-aminoethoxy)-3-methoxyphenylacetamide;
N-{3-(3,4-dichlorophenyl)propyl}-4-(2-aminoethoxy)-3-methoxyphenylacetamide;
N-{3-(4-fluorophenyl)propyl}-4-(2-aminoethoxy)-3-methoxyphenylacetamide;
N-{3-(3,4-methylenedioxyphenyl)propyl}-4-(2-aminoethoxy)-3-methoxyphenylacetamide;
N-{3-(3-methoxyphenyl)propyl}-4-(2-aminoethoxy)-3-methoxyphenylacetamide;
N-{3-(3-benzyloxyphenyl)propyl}-4-(2-aminoethoxy)-3-methoxyphenylacetamide;
N-{3-(3,4-dimethoxyphenyl)propyl}-4-(2-aminoethoxy)-3-methoxyphenylacetamide; and
N-{3-(3-trifluoromethylphenyl)propyl}-4-(2-aminoethoxy)-3-methoxyphenylacetamide.

As will be amply demonstrated below, 4-(2-aminoethoxy) phenylacetamide derivatives of the formula (I) according to the present invention, which have various substitutents of ω-phenylalkyl group on the carbonyl radical, and pharmaceutically acceptable salts thereof, have superior anti-inflammatory and analgesic activities to any compounds known in the prior art.

The following Preparation Examples illustrate how the starting materials can be prepared.

PREPARATION EXAMPLE 1

Synthesis of 3-(3,4-dimethylphenyl)propylamine

To a solution of 70.0 ml of diethyl malonate dissolved in 400 ml of dry ethanol was added 10.0 g of metalic sodium. The reaction mixture was stirred for 30 minutes and cooled to 0° C; and 66.5 g of 3,4-dimethylbenzyl chloride was added thereto. This reaction mixture was stirred for 1 hour at room temperature, heated at the boiling temperature for 4 hours and concentrated under reduced pressure to produce residues, which were dissolved in ethyl ether. This ethereal solution was washed with water. To the residues obtained after a further concentration of the organic phase were added 500 ml of water and 170 g of KOH; and this mixture was heated at the boiling temperature for 24 hours. This mixture was concentrated under reduced pressure until about a half of the amount remained, and 200 ml of sulfuric acid was then slowly added thereto. The resultant solution was heated at the boiling temperature for 24 hours, extracted twice with 300 ml of ethyl ether and evaporated under reduced pressure to obtain solids, which were recrystallized from boiling hexane to provide 42.1 g of 3-(3,4-dimethylphenyl)propanoic acid as a white solid (yield 55%), having the characteristics of: m.p. 82° C.; NMR(CDCl$_3$, 300 MHz) δ2.22(s, 3H, CH$_3$), 2.24(s, 3H, CH$_3$), 2.66(t, J=8 Hz, 2H, ArCH$_2$), 2.89(t, J=8 Hz, 2H, CH$_2$CO), 6.93~7.70(m, 3H, ArH).

A mixture of 18.5 g of 3-(3,4-dimethylphenyl)-propanoic acid obtained above and 50 ml of thionyl chloride was heated to reflux for 2 hours and concentrated under reduced pressure to give residues, which were dissolved in 100 ml of ethyl ether. The ethereal solution was added to a mixture of 200 ml of ethyl ether, 150 ml of water and 50 ml of 30% aqueous ammonia solution with stirring. The organic layer was separated and the remaining aqueous layer was extracted twice with 150 ml of dichloromethane. The organic layers were combined and concentrated under reduced pressure to give residues, which were dissolved in 150 ml of tetrahydrofuran. The solution was added to a mixture of 8.0 g of LiAlH$_4$ and 200 ml of tetrahydrofuran; and the resultant solution was heated at the boiling temperature for 6 hours. To this reaction mixture were slowly added 30 ml of 30% NaOH aqueous solution and 20 ml of water. The tetrahydrofuran layer was separated from the mixture and the remaining solids were dissolved in 300 ml of water. The aqueous solution was extracted twice with 200 ml of ethyl ether. The previously separated tetrahydrofuran solution and the ethyl ether solution were combined and then concentrated. The residues so obtained were distilled under reduced pressure to obtain 13.4 g of 3-(3,4-dimethylphenyl)propylamine (yield 70%), having the characteristics of: b.p. 140°–150° C./0.5 mmHg; NMR(CDCl$_3$, 300 MHz) δ1.32 (br s, 2H, NH$_2$), 1.74(quint, J=7 Hz, 2H, CH$_2$), 2.23(s, 3H, CH$_3$), 2.24(s, 3H, CH$_3$), 2.59(t, J=7 Hz, 2H, ArCH$_2$), 2.72(t, J=7 Hz, 2H, CH$_2$N), 6.91–7.06(m, 3H, ArH).

PREPARATION EXAMPLE 2

Synthesis of 3-(3-methylphenyl)propylamine

The procedures of Preparation Example 1 were repeated except that 3,4-dimethylbenzyl chloride was replaced with 3-methylbenzyl chloride to obtain the title compound (yield 82%), having the characteristics of: b.p. 150° C./0.3 mmHg; NMR(CDCl$_3$) δ1.20(br s, 2H, NH$_2$), 1.76(m, 2H, CH$_2$), 2.33(s, 3H, ArCH$_3$), 2.61(t, J=7 Hz, 2H, ArCH$_2$), 2.72(t, J=7 Hz, 2H, CH$_2$NH$_2$), 6.48–7.20(m, 4H, ArH).

PREPARATION EXAMPLE 3

Synthesis of 3-(4-methylphenyl)propylamine

The procedures of Preparation Example 1 were repeated except that 3,4-dimethylbenzyl chloride was replaced with 4-methylbenzyl chloride to obtain the title compound (yield 73%), having the characteristics of: b.p. 130° C./0.4 mmHg; NMR(CDCl$_3$) δ1.55(br s, 2H, NH$_2$), 1.75(m, 2H, CH$_2$), 2.32(s, 3H, ArCH$_3$), 2.61(t, J=7 Hz, 2H, ArCH$_2$), 2.72(t, J=7 Hz, 2H, CH$_2$NH$_2$), 7.01(s, 4H, ArH).

PREPARATION EXAMPLE 4

Synthesis of 3-(3,5-dimethylphenyl)propylamine

The procedures of Preparation Example 1 were repeated except that 3,4-dimethylbenzyl chloride was replaced with 3,5-dimethylbenzyl chloride (yield 71%), having the characteristics of: b.p. 150° C./0.3 mmHg; NMR(CDCl$_3$) δ1.48(br s, 2H, NH$_2$), 1.74(quint, J=7 Hz, 2H, CH$_2$), 2.21(s, 6H, 2ArCH$_3$), 2.56(t, J=7 Hz, 2H, ArCH$_2$), 2.70(t, J=7 Hz, CH$_2$NH$_2$), 6.81(s, 3H, ArH).

PREPARATION EXAMPLE 5

Synthesis of 2-(3,4-dimethylphenyl)ethylamine

To a solution of 6.8 g of 90% sodium cyanide dissolved in 6.5 ml of distilled water while being subjected to heating was added a solution of 15.5 g of 3,4-dimethylbenzyl chloride in 20 ml of dry ethanol; and the resultant mixture was heated at the boiling temperature for 10 hours and then cooled to room temperature. This solution was added to 50 ml of distilled water and extracted twice with 150 ml of ethyl ether. The organic solvent was removed to obtain 11.5 g(yield 79%) of 3,4-dimethylbenzyl cyanide, which was dissolved in 50 ml of dry tetrahydrofuran. The organic solution was slowly added to a dispersion of 6.0 g of LiALH$_4$ suspended in 150 ml of dry tetrahydrofuran; and the mixture was heated at the boiling point for 14 hours. This reaction mixture was cooled to room temperature; and 16 ml of 1N NaOH and 8 ml of distilled water were slowly added thereto. Thereafter, this reaction mixture was filtered through a Celite layer to obtain solids, which were dissolved in a mixture of 250 ml of ethyl ether and 250 ml of ethyl alcohol and filtered. After the filtrate was basified with 5N NaOH aqueous solution and extracted with dichloromethane(200 ml×2), the solvent was evaporated and distilled under reduced pressure to provide 5.6 g(yield 48%) of the title compound.

PREPARATION EXAMPLE 6

Synthesis of 3-(4-chlorophenyl)propylamine

A mixture of 6.75 g of 4-chlorocinnamic acid and 0.3 g of CuSO$_4$.5H$_2$O dispersed in 50 ml of ethyl alcohol was stirred at room temperature for 10 minutes; and 23 ml of 95% hydrazine was added thereto. This reactant was stirred for 18 hours with air bubbling at the speed of 1 L/min. The reaction mixture was filtered through a Celite layer and 30 ml of 1N NaOH was added thereto. The solution was washed twice with 30 ml of dichloromethane, acidified with concentrated hydrochloric acid, extracted with 100 ml of ethyl acetate four times and dried over magnesium sulfate. The solvent was evaporated to give 6.05 g(yield 89%) of 3-(4-chlorophenyl)propanoic acid as a yellow solid.

5.90 g of 3-(4-chlorophenyl) propanoic acid obtained above was dissolved in 6 ml of thionyl chloride, heated to reflux for 2 hours and concentrated under reduced pressure. The residues thus obtained were dissolved in 100 ml of dry ethyl ether and the solution was added dropwise to 150 ml of NH$_4$OH in an ice bath. The resultant solution was stirred at room temperature for 1 hour and extracted twice with 200 ml of dichloromethane. The organic phase was washed with 100 ml of a saturated sodium hydrogen carbonate aqueous solution and dried over magnesium sulfate. The solvent was evaporated to provide 4.62 g(yield 78%) of 3-(4-chlorophenyl)propanamide.

4.62 g of amide obtained above was dissolved in 50 ml of dry tetrahydrofuran; and the solution was slowly added to a dispersion of 2.4 f of LiAlH$_4$ in 150 ml of dry tetrahydrofuran with reflux for 2 hours. The reaction mixture was cooled to room temperature, treated with 10 ml of 1N NaOH and filtered through a Celite layer to give solids, which were dissolved in 150 ml of distilled water and then filtered through a Celite layer. The filtrate so obtained was extracted with ethyl ether(100 ml×3). The combined organic layer was dried over magnesium sulfate, concentrated and distilled under reduced pressure to provide 3.12 g(yield 73%) of the title compound as a colorless liquid: b.p. 140° C./3.4 mmHg.

PREPARATION EXAMPLE 7

Synthesis of 3-(4-fluorophenyl)propylamine

The procedures of Preparation Example 6 were repeated except that 4-chlorocinnamic acid was replaced with 4-fluorocinnamic acid to obtain the title compound, having the characteristics of: NMR (CDCl$_3$) δ1.35(s, 2H, NH$_2$), 1.73(m, 2H, CH$_2$), 2.65(m, 4H, 2CH$_2$), 6.71(m, 2H, ArH), 7.03(m, 2H, ArH).

PREPARATION EXAMPLE 8

Synthesis of 3-(2,4-dichlorophenyl)propylamine

The procedures of Preparation Example 6 were repeated except that 4-chlorocinnamic acid was replaced with 2,4-dichlorocinnamic acid to obtain the title compound, having the characteristics of: b.p. 116° C./0.75 mmHg; NMR(CDCl$_3$) δ1.13(s, 2H, NH$_2$), 1.81(m, 2H, CH$_2$), 2.78(m, 4H, 2CH$_2$), 7.27(m, 3H, ArH)

PREPARATION EXAMPLE 9

Synthesis of 3-(3,4-dichlorophenyl)propylamine

The procedures of Preparation Example 6 were repeated except that 4-chlorocinnamic acid was replaced with 3,4-dichlorocinnamic acid to obtain the title compound, having the characteristics of: NMR (CDCl$_3$) δ1.45(s, 2H, NH$_2$), 1.72(quint, J=7.4 Hz, 2H, CH$_2$), 2.60(t, J=7.8 Hz, 2H, CH$_2$N), 2.70(t, J=7.1 Hz, 2H, ArCH$_2$), 7.00(dd, J=2.1, 8.1 Hz, 1H, ArH), 7.26(d, J=2.0 Hz, 1H, ArH), 7.31(d, J=8.2 Hz, 1H, ArH).

PREPARATION EXAMPLE 10

Synthesis of 3-(3,4-methylenedioxyphenyl)propylamine

To a solution of 10.0 g of 3,4-methylenedioxycinnamic acid dissolved in 130 ml of 10% NaOH and 80 ml of distilled water was added 1.0 g of 5% Pd-C. This mixture was reacted at 40 psi until the consumption of hydrogen gas was ceased and then filtered through a Celite layer. The filtrate was acidified with concentrated hydrochloric acid, allowed to be cooled and filtered to give solids. The obtained solids were washed twice with 100 ml of cold water and dried to provide 9.8 g(yield 97%) of 3-(3,4-methylenedioxyphenyl) propanoic acid, having the characteristics of: NMR(CDCl$_3$, 200 MHz) δ2.62(t, J=7 Hz, 2H, CH$_2$), 2.88(t, J=7 Hz, 2H, CH$_2$N), 5.9'(s, 2H, CH$_2$O$_2$), 6.63-6.76(s, 3H, ArH).

A mixture of 8.23 g of the propanoic acid obtained above and 5.3 ml of thionyl chloride was heated to reflux for 2 hours and concentrated under reduced pressure to give residues, which were dissolved in 100 ml of dry ethyl ether. This solution was slowly added dropwise to 150 ml of NH$_4$OH solution in an ice bath. The resultant mixture was stirred at room temperature for 1 hour, extracted with ether(200 ml×3) and dried over magnesium sulfate; and the solvent was removed therefrom to provide 7.89 g(yield 96%) of 3-(3,4-methylenedioxyphenyl)propanamide.

6.0 g of the above amide was dissolved in 100 ml of dry tetrahydrofuran, which was added dropwise to a suspension of 2.4 g of LiAlH$_4$ in 150 ml of dry tetrahydrofuran. The reaction mixture was refluxed for 2 hours and 10 ml of 1N NaOH was added thereto. The mixture was filtered through a Celite layer to give solids, which were dissolved in 200 ml of distilled water. This solution was extracted twice with 200 ml of ethyl ether. The combined organic phase was dried over magnesium sulfate, concentrated and distilled under reduced pressure to provide 4.71 g(yield 85%) of 3-(3,4-methylenedioxyphenyl) propylamine, having the characteristics of: NMR(CDCl$_3$, 200 MHz) δ1.34 (br s, 2H, NH$_2$), 1.72(m, J=7 Hz, 2H, CH$_2$), 2.57(t, J=7 Hz, 2H, CH$_2$), 2.71(t, J=7 Hz, 2H, CH$_2$N), 5.91(s, 2H, CH$_2$O$_2$), 6.59-6.74(s, 3H, ArH).

PREPARATION EXAMPLE 11

Synthesis of 3-(3-trifluoromethylphenyl)propylamine

The procedures described in Preparation Example 10 above were repeated except that 3,4-methylenedioxycinnamic acid was replaced with 3-trifluoromethylcinnamic acid to obtain the title compound, having the characteristics of: NMR(CDCl$_3$) δ1.40-2.10(m, 4H, CH$_2$, NH$_2$), 2.40-2.90(m, 4H, 2CH$_2$), 7.30(s, 4H, ArH).

PREPARATION EXAMPLE 12

Synthesis of 3-(3-benzyloxyphenyl)propylamine

The procedures described in Preparation Example 10 above were repeated except that 3,4-methylenedioxycinnamic acid was replaced with 3-benzyloxycinnamic acid to obtain the title compound.

PREPARATION EXAMPLE 13

Synthesis of 3-(3-methoxyphenyl)propylamine

The procedures described in Preparation Example 10 above were repeated except that 3,4-methylenedioxycinnamic acid was replaced with 3-methoxycinnamic acid to obtain the title compound, having the characteristics of: NMR(CDCl$_3$) δ1.24(s, 2H, CH$_2$), 1.72(m, 2H, CH$_2$), 2.61(m, 4H, 2CH$_2$), 3.68(s, 3H, OCH$_3$), 6.71(m, 3H, ArH), 7.18(m, 1H, ArH).

PREPARATION EXAMPLE 14

Synthesis of 3-(3,4-dimethoxyphenyl)propylamine

The procedures described in Preparation Example 10 above were repeated except that 3,4-methylenedioxycinnamic acid was replaced with 3,4-dimethoxycinnamic acid to obtain the title compound (yield 73%).

PREPARATION EXAMPLE 15

Synthesis of 3-(4-methoxyphenyl)propylamine

The procedures described in Preparation Example 10 above were repeated except that 3,4-methylenedioxycinnamic acid was replaced with 4-methoxycinnamic acid to obtain the title compound(yield 94%), having the characteristics of: NMR(CDCl$_3$) δ1.21(s, 2H, NH$_2$), 1.71 (m, 2H, CH$_2$), 2.57(t, J=7 Hz, 2H, CH$_2$), 2.69(t, J=7 Hz, 2H, CH$_2$), 3.75(s, 3H, OCH$_3$), 6.81-7.10(m, 4H, ArH).

PREPARATION EXAMPLE 16

Synthesis of 4-(3-methylphenyl)butylamine

A mixture of 14.0 g of 3-methylbenzyl chloride and 50.0 g of ethyl acrylate dissolved in 300 ml of dry toluene was heated to 110° C. Separately, 3.0 g of 2,2'-azobisisobutyronitrile(AIBN) and 32.0 g of tri-n-butyltin hydride were dissolved in 200 ml of dry toluene, which was added to the above mixture over a period of 2 hours. This reaction mixture was further heated at the boiling temperature for 2 hours and then cooled to the ambient temperature. The residues obtained after removing the solvent from the mixture were purified by silica gel column chromatography to provide ethyl-4-(3-methylphenyl)butanoate.

Hereto was introduced 100 ml of 10% KOH aqueous solution; and the mixture was heated at the boiling temperature for 12 hours. The organic layer was washed with 50 ml of ethyl ether, and the aqueous layer was acidified with concentrated hydrochloric acid and extracted with ethyl ether(100 ml×3). The organic solvent was removed under a reduced pressure to provide 9.6 g(yield 55%) of 4-(3-methylphenyl)butanoic acid in the form of an emulsion.

A mixture of 3.3 g of 4-(3-methylphenyl)butanoic acid obtained above and 10 ml of thionyl chloride was heated at the boiling point for 2 hours and concentrated under reduced pressure to obtain residues, which were dissolved in 50 ml of ethyl ether. This solution was added to a mixture of 60 ml of ethyl ether, 300 ml of water and 20 ml of 30% aqueous ammonia solution with stirring. The organic layer was extracted with dichloromethane(50 ml×2). The combined organic layer was evaporated under reduced pressure to give residues, which were dissolved in 40 ml of tetrahydrofuran. This solution was mixed with a mixture of 0.94 g of LiAlH$_4$ and 60 ml of tetrahydrofuran, which reaction mixture was then heated at the boiling point for 5 hours. To the above mixture was slowly added 10 ml of 10% NaOH solution. The tetrahydrofuran layer was separated; and the residues were dissolved in 100 ml of water. This aqueous solution was extracted with ethyl ether(50 ml×2). The ethyl ether layer and the separated tetrahydrofuran layer were combined and concentrated under reduced pressure. The residues so obtained were distilled under reduced pressure to provide 1.48 g(yield 79%) of the title compound, having the characteristics of: b.p. 145°-150° C./0.35 mmHg; NMR(CDCl$_3$) δ1.49 (m, 2H, NH$_2$), 1.59-1.67(m, 4H, 2CH$_2$), 2.33(s, 3H, ArCH$_3$), 2.59 (t, J=7 Hz, 2H, ArCH$_2$), 2.70(t, J=7 Hz, 2H, NHCH$_2$), 6.97-7.20(m, 4H, ArH).

PREPARATION EXAMPLE 17

Synthesis of 4-(3,4-dimethylphenyl)butylamine

The title compound was prepared according to the procedures described in Preparation Example 16 above except for using 3,5-dimethylbenzyl chloride instead of 3-methylbenzyl chloride.

PREPARATION EXAMPLE 18

Synthesis of 3-benzyloxy-4-hydroxyphenylacetic acid

To a solution of 5.79 g of 3,4-dihydroxylphenyl acetic acid ethyl ester dissolved in dry acetone were added 4.48 g of potassium carbonate and 4.15 ml of benzyl bromide. The mixture was heated to reflux until the starting materials were exhausted; and then the solvent was distilled off under reduced pressure. To the residues thus obtained was added 50 ml of water; and the mixture was acidified with concentrated hydrochloric acid and extracted with dichloromethane. The organic layer was dried over magnesium sulfate and evaporated under reduced pressure to obtain residues, which were purified by chromatography to provide 3.80 g (yield 45%) of 3-benzyloxy-4-hydroxyphenylacetic acid ethyl ester, having the characteristics of: NMR(CDCl$_3$, 200 MHz) δ1.24(t, J=7 Hz, 3H, CH$_3$), 3.45(s, 2H, CH$_2$CO), 4.12(q, J=7 Hz, 2H, OCH$_2$), 5.05(s, 2H, CH$_2$Ph), 6.77-7.35(m, 6H, ArH).

5.35 g of the ester obtained above was added to a mixture of 50 ml of water and 1.49 g of sodium hydroxide. The resultant solution was refluxed for 2.5 hours, acidified with concentrated hydrochloric acid and evaporated under reduced pressure to give solids, which were purified by Soxhlet extraction apparatus to provide 4.27 g(yield 89%) of the desired compound as a yellow solid, having the characteristics of: m.p. 130°-133° C.; NMR(CDCl$_3$, 200 MHz) δ3.45(s, 2H, CH$_2$Ar), 5.09 (s, 2H, OCH$_2$), 6.75-7.40(m, 6H, ArH).

The following Examples illustrate how some of the compounds of formula(I) can be prepared.

EXAMPLE 1

Synthesis of N-{3-(3,4-dimethylphenyl)propyl}-4-(2-aminoethoxy)-3-methoxyphenylacetamide Step 1) Synthesis of N-{3-(3,4-dimethylphenyl)propyl}-4-hydroxy-3-methoxyphenylacetamide A mixture of 1.39 g of 3-(3,4-dimethylphenyl)propylamine obtained in Preparation Example 1, 1.50 g of 4-hydroxy-3-methoxyphenylacetic acid and 0.60 g of powdered 4 Å molecular sieve was stirred for 4 hours at a temperature within the range of 150°-160° C. and dissolved in 10 ml of dichloromethane. The resultant mixture was purified by column chromatography to provide 2.43 g(yield 90%) of the title compound, having the characteristics of: NMR(CDCl$_3$) δ1.72(m, 2H, CH$_2$), 2.21(s, 6H, 2ArCH$_3$), 2.49(t, J=7 Hz, 2H, ArCH$_2$), 3.22(q, J=7 Hz, 2H, ArCH$_2$), 3.47(s, 2H, CH$_2$CO), 3.87(s, 3H, OCH$_3$), 5.44 (s, 1H, NH), 5.78(s, 1H, OH), 6.68-7.04(m, 6H, ArH).

Step 2) Synthesis of N-{3-(3,4-dimethylphenyl)propyl}-4-(2-bromoethoxy)-3-methoxyphenylacetamide The amide obtained in step 1 was dissolved in a mixed solvent of 60 ml of tetrahydrofuran and 10 ml of 2,2-dibromethane; and then 2.2 g of 50% NaH was added thereto. The reaction mixture was heated at the boiling temperature for 12 hours and charged into 200 ml of water. This was extracted with dichloromethane(150 ml×2) and evaporated under reduced pressure to remove the solvent. The residue so obtained was purified by column chromatography and recrystallized from dichloromethane-hexane to provide 1.53 g(yield 63%) of the title compound, having the characteristics of: m.p. 105° C.; NMR(CDCl$_3$) δ1.73 (quint, J=7 Hz, 2H, CH$_2$), 2.21(s, 6H, 2ArCH$_3$), 2.50(t, J=7 Hz, 2H, ArCH$_2$), 3.22(q, J=7 Hz, 2H, NCH$_2$), 3.48(s, 2H, CH$_2$CO), 3.66(t, J=6 Hz, 2H, CH$_2$Br), 3.86(s, 3H, OCH$_3$), 4.32(t, J=6 Hz, 2H, OCH$_2$), 5.38(br s, 1H, NH), 6.73-7.05(m, 6H, ArH).

Step 3) Synthesis of N-{3-(3,4-dimethylphenyl)propyl}-4-(2-azidoethoxy)-3-methoxyphenylacetamide To a solution containing 1.16 g of 4-(2-bromoethoxy)-phenylacetamide compound obtained in step 2 dissolved in 20 ml of benzene were added 0.90 g of NaN$_3$ and 0.17 g of n-Bu$_4$NBr. The reaction mixture was heated at the boiling temperature for 24 hours, diluted with 100 ml of dichloromethane and washed with 100 ml of water. The solvent was removed under reduced pressure to give residues, which were purified by column chromatography and recrystallized from dichloromethane-hexane to provide 1.03 g(yield 97%) of the title compound, having the characteristics of: m.p. 105° C.; NMR(CDCl$_3$) δ1.73 (quint, J=7 Hz, 2H, CH$_2$), 2.22(s, 6H, 2ArCH$_3$), 2.50(t, J=7 Hz, 2H, ArCH$_2$), 3.23(q, J=7 Hz, 2H, NCH$_2$), 3.49(s, 2H, CH$_2$CO), 3.64(t, J=5 Hz, 2H, OCH$_2$), 3.86(s, 3H, OCH$_3$), 4.18(t, J=5 Hz, 2H, CH$_2$N$_3$), 5.40(br s, 1H, NH), 6.73-7.06(m, 6H, ArH).

Step 4) Synthesis of N-{3-(3,4-dimethylphenyl)-propyl}-4-(2-aminoethoxy)-3-methoxyphenylacetamide To a solution containing 1.00 g of 4-(2-azidoethoxy)-phenylacetamide compound obtained in step 3 dissolved in 100 ml of ethyl acetate was added 0.30 g of 10% Pd-C. This reaction mixture was reacted for 5 hours at the hydrogen pressure of about 40 psi, filtered through a Celite layer to remove Pd-C and evaporated under reduced pressure to remove the solvent. The residues so obtained were recrystallized from dichloromethane-hexane to provide 0.88 g(yield 94%) of the desired compound, having the characteristics of: m.p. 125° C.; NMR(CDCl$_3$) $\delta$1.72(m, 4H, CH$_2$, NH$_2$), 2.21(s, 6H, 2ArCH$_3$), 2.49(t, J=7 Hz, 2H, ArCH$_2$), 3.11(q, J=5 Hz, 2H, OCH$_2$), 3.22(q, J=7 Hz, 2H, NCH$_2$), 3.49(s, 2H, CH$_2$CO), 3.85(s, 3H, OCH$_3$), 4.04(t, J=5 Hz, 2H, CH$_2$N), 5.42(br s, 1H, NH), 6.71–7.03(m, 6H, ArH).

EXAMPLES 2 TO 35

In accordance with the procedures described in Example 1, further compounds were prepared. Their particulars are as shown in Table 1.

EXAMPLE 36

Synthesis of N-{3-(3,4-dimethylphenyl)propyl}-4-(2-aminoethoxy)-3-hydroxyphenylacetamide Step 1) Synthesis of N-{3-(3,4-dimethylphenyl)-propyl}-3-benzyloxy-4-hydroxyphenylacetamide The procedures described in step 1 of Example 1 were repeated except that 4-hydroxy-3-methoxyphenylacetic acid was replaced with 3-benzyloxy-4-hydroxyphenylacetic acid to obtain the title compound (yield 87%), having the characteristics of: m.p. 63°–66° C.; NMR(CDCl$_3$, 200 MHz) $\delta$1.70(m, J=7 Hz, 2H, CH$_2$), 2.19(s, 6H, 2CH$_3$), 2.45(t, J=7 Hz, 2H, CH$_2$), 3.18(q, J=5.1 Hz, 2H, CH$_2$N), 3.41(s, 2H, CH$_2$Ar), 5.02(s, 2H, CH$_2$), 5.63(b, 1H, NH), 6.68–7.35(m, 6H, ArH).

Step 2) Synthesis of N-{3-(3,4-dimethylphenyl)-propyl}-3-benzyloxy-4-(2-bromoethoxy)phenylacetamide The procedures described in step 2 of Example 1 were repeated to obtain the title compound (yield 85%) having the characteristics of: m.p. 73°–75° C.; NMR(CDCl$_3$, 200 MHz) $\delta$1.71(m, J=7 Hz, 2H, CH$_2$), 2.22(s, 6H, 2CH$_3$), 2.50(t, J=7 Hz, 2H, CH$_2$), 3.19(q, J=6.7 Hz, 2H, CH$_2$NH), 3.45(s, 2H, CH$_2$CO), 3.65(t, J=6.4 Hz, 2H, CH$_2$Br), 4.35(t, J=6.4 Hz, 2H, CH$_2$O), 5.14(s, 2H, OCH$_2$Ph), 5.25(b, 1H, NH), 6.73–7.47(m, 6H, ArH).

Step 3) Synthesis of N-{3-(3,4-dimethylphenyl)-propyl}-3-benzyloxy-4-(2-azidoethoxy)phenylacetamide The procedures described in step 3 of Example 1 were repeated to obtain the title compound (yield 84%), having the characteristics of: m.p. 105°–106° C.; NMR(CDCl$_3$, 200 MHz) $\delta$1.64(m, J=6.5 Hz, 2H, CH$_2$), 2.21(s, 6H, 2CH$_3$), 2.49(t, J=8 Hz, 2H, CH$_2$), 3.20(q, J=6.8 Hz, 2H, CH$_2$N), 3.45(s, 2H, CH$_2$Ar), 3.61(t, J=5 Hz, 2H, CH$_2$N$_3$), 4.20(t, J=5.1 Hz, 2H, OCH$_2$), 5.11(s, 2H, OCH$_2$Ph), 5.30(b, 1H, NH), 6.74–7.45(m, 6H, ArH).

Step 4) Synthesis of N-{3-(3,4-dimethylphenyl)-propyl}-4-(2-aminoethoxy)-3-hydroxyphenylacetamide The procedures described in step 4 of Example 1 were repeated to obtain the title compound(yield 87%), having the characteristics of: m.p. 144°–147° C.; NMR(CDCl$_3$, 200 MHz) $\delta$1.65(m, J=6.6 Hz, 2H, CH$_2$), 2.10(s, 6H, 2CH$_3$), 2.40(t, J=8 Hz, 2H, CH$_2$), 2.95(t, J=5 Hz, 2H, CH$_2$N), 3.18(m, J=6.7 Hz, 2H, CH$_2$NCO), 3.35(s, 2H, CH$_2$Ar), 3.92(t, J=5 Hz, 2H, OCH$_2$), 5.85(b, 1H, NH), 6.68–7.31(m, 6H, ArH).

EXAMPLES 37 TO 39

In accordance with the procedures described in Example 36, various compounds were prepared. The results are shown in Table 1.

EXAMPLE 40

Synthesis of N-{3-(3,4-dimethylphenyl)propyl}-4-(2-aminoethoxy)-3-aminophenylacetamide Step 1) Synthesis of N-{3-(3,4-dimethylphenyl)-propyl}-4-hydroxy-3-nitrophenylacetamide A mixture of 7.0 g of 4-hydroxy-3-nitrophenylacetic acid and 8.11 g of (COCl)$_2$ suspended in 15 ml of dichloromethane was heated to reflux for 2 hours and concentrated under reduced pressure to give residues, which were dissolved in dichloromethane. Hereto 4.14 g of triethylamine and 6.37 g of 3-(3,4-dimethylphenyl)-propylamine were added, and the mixture was stirred at room temperature for 5 hours. The solvent was evaporated off and the obtained residues were purified by chromatography and recrystallized from dichloromethanehexane to provide 10.98 g(yield 90%) of the title compound, having the characteristics of: m.p. 103° C.; NMR(CDCl$_3$, 200 MHz) $\delta$1.77(m, J=7 Hz, 2H, CCH$_2$C), 2.23(s, 6H, CH$_3$), 2.55(t, J=8 Hz, 2H, CH$_2$Ar), 3.15(t, J=5.0 Hz, 2H, CH$_2$NH$_2$), 3.29(q, J=6.7 Hz, 2H, NHCH$_2$), 3.46 (s, 2H, CH$_2$CO), 4.15(t, J=5.0 Hz, 2H, OCH$_2$), 5.40(b, 1H, NH), 6.86–7.75(m, 6H, ArH).

Step 2) Synthesis of N-{3-(3,4-dimethylphenyl)-propyl}-4-(2-bromoethoxy)-3-nitrophenylacetamide The procedures described in step 2 of Example 1 were repeated to obtain the title compound (yield 94%), having the characteristics of: m.p. 93° C.; NMR(CDCl$_3$, 300 MHz) $\delta$1.80(quint, J=7 Hz, 2H, CH$_2$), 2.23 (s, 6H, 2CH$_3$), 2.57(t, J=8 Hz, 2H, CH$_2$Ar(CH$_3$)$_2$), 3.25(q, J=6.8 Hz, 2H, CH$_2$NH), 3.46(s, 2H, CH$_2$CO), 3.68(t, J=6.5 Hz, 2H, CH$_2$Br), 3.45 (t, J=6.5 Hz, CH$_2$O), 5.38(br, 1H, NH), 6.86–7.72(m, 6H, ArH).

Step 3) Synthesis of N-{3-(3,4-dimethylphenyl)-propyl}-4-(2-azidoethoxy)-3-nitrophenylacetamide The procedures described in step 3 of Example 1 were repeated to obtain the title compound(yield 97%), having the characteristics of: m.p. 89° C.; NMR(CDCl$_3$, 300 MHz) $\delta$1.80(quint, J=7 Hz, 2H, CH$_2$), 2.27(s, 6H, 2CH$_3$), 2.57(t, J=8 Hz, 2H, 2CH$_3$), 3.27(q, J=6.8 Hz, 2H, CH$_2$NCO), 3.48(s, 2H, CH$_2$CO), 3.69(t, J=4.9 Hz, 2H, CH$_2$N$_2$), 4.27(t, J=4.9 Hz, 2H, CH$_2$O), 5.40(br, 1H, NH), 6.88–7.75(m, 6H, ArH).

Step 4) Synthesis of N-{3-(3,4-dimethylphenyl)-propyl}-4-(2-aminoethoxy)-3-aminophenylacetamide The procedures described in step 4 of Example 1 were repeated to obtain the title compound(yield 94%), having the characteristics of: m.p. 98° C.; NMR(CDCl$_3$, 300 MHz) $\delta$1.72(quint, J=7 Hz, 2H, CH$_2$), 2.20(s, 6H, 2CH$_3$), 2.48(t, J=8 Hz, 2H, 2CH$_3$), 3.10(t, J=5.2 Hz, 2H, CH$_2$NH$_2$), 3.20(q, J=6.7 Hz, 2H, CH$_2$NCO), 3.42(s, 2H, CH$_2$CO), 4.03(t, J=5.2 Hz, 2H, CH$_2$O), 5.44(br, 1H, NH), 6.52–7.29(m, 6H, ArH).

EXAMPLES 41-49

Further compounds of the formula(I) were prepared in accordance with the procedures described in Example 40. The results are shown in Table 1.

EXAMPLE 50

Synthesis of N-{3-(3,4-dimethylphenyl)propyl}-4-(2-aminoethoxy)-3-nitrophenylacetamide To a solution of 685 mg of azide compound obtained in step 3 of Example 40 dissolved in 6 ml of tetrahydrofuran was added 437 mg of triphenylphosphine. This reaction mixture was stirred at room temperature for 2 hours and 0.1 ml of water was added thereto. This mixture was stirred at room temperature for 4 hours and evaporated under reduced pressure to remove the solvent. The residue was purified by chromatoghaphy and recrystallized from dichloromethanehexane to provide 525 mg(yield 82%) of the desired compound as a yellow precipitate, having the characteristics of: m.p. 98° C.; NMR (CDCl$_3$, 200 MHz) $\delta$1.77(m, J=7 Hz, 2H, CCH$_2$C), 2.23(s, 6H, CH$_3$), 2.55(t, J=8 Hz, 2H, CH$_2$Ar), 3.15(t, J=5.0 Hz, 2H, CH$_2$NH$_2$), 3.29 (q, J=6.7 Hz, 2H, NHCH$_2$), 3.46(s, 2H, CH$_2$CO), 4.15(t, J=5.0 Hz, 2H, OCH$_2$), 5.40(br s, 1H, NH), 6.86-7.75(m, 6H, ArH).

EXAMPLES 51-56

Further compounds were prepared in accordance with the procedures described in Example 50. The results are shown in Table 1.

The following Use Examples illustrate how some of the pharmaceutical compositions of the present invention can be prepared.

USE EXAMPLE 1

Tablets were prepared by using conventional methods, e.g., mixing and direct compression, and formulated as follows:

| Ingredients | mg per tablet |
|---|---|
| The Compound of Example 1 | 10 |
| Compressible sugar (Di-pac) | 400 |
| Sodium starch glycolate | 35 |
| Silica Gel (Syloid 244) | 15 |

One tablet was administered orally to a patient(male; age: 42; weight: 67 kg) in need of analgesia two times daily to successfully provide the effect of general analgesia.

USE EXAMPLE 2

Capsules for oral administration were prepared by combining the following ingredients:

| Ingredients | Amount |
|---|---|
| The Compound of Example 8 | 20 mg |
| Sesame oil | 100 ml |

The compound of Example 8 was dissolved in sesame oil with the aid of sonication and was packaged in soft gelatin capsules using the common methods known in the art. Two of the resulting capsules, each containing 27 mg of the composition, were administered to a 63 Kg male(age: 35) in need of treatment, producing the effects of analgesia and reducing inflammation.

USE EXAMPLE 3

Syrup for oral administration was prepared by combining the following ingredients:

| Ingredients | Amount |
|---|---|
| The Compound of Example 1 | 250 g |
| Benzoic Acid Solution | 20 ml |
| Compound Tartrative Solution | 10 ml |
| Water for preparations | 20 ml |
| Lemon syrup | 200 ml |
| Syrup | to 1000 ml |

The above ingredients were mixed to produce a syrup which was packaged under a sterile condition in 6 oz. bottles. One teaspoon of this formulation was administrated to a 70 kg male adult (age: 27), reducing inflammation and producing analgesia.

USE EXAMPLE 4

Injectable compositions were prepared as follows:

| Ingredients | Amount |
|---|---|
| Composition 1: | |
| The Compound of Example 8 | 0.01% |
| Aqueous Acetic Acid (1.30%) | 95.45% |
| Dextrose | 4.54% |
| Composition 2: | |
| The Compound of Example 8 | 0.05% |
| Aqueous Sodium Acetate (1.18%) | 85.95% |
| Aqueous Acetic Acid (2.0%) | 10.00% |
| Benzyl alcohol | 4.04% |

The injection of 0.5 ml of Composition 2 prior to oral surgery for a third molar extraction of a female adult(-weight: 52 kg; age: 29) successfully provided local anesthesia during the surgery.

USE EXAMPLE 5

A composition for topical administration was prepared by combining the following ingredients:

| Ingredients | Amount |
|---|---|
| The Compound of Example 1 | 4 g |
| Glycerol | 12 ml |
| Purified water | 200 ml |

The compound of Example 1 was dissolved in a solution containing the other ingredients. Application of 0.4 ml of the resulting liquid to a 80 cm$^2$ portion of the forearm of a 60 kg male adult produced local analgesia which lasted for two days. Little or no skin irritation was observed.

TESTS OF THE ACTIVITY

Physiological activities of the compounds prepared above were measured by employing the following methods.

1. Writing Test

1) Animals tested

The KTC-ICR mice derived from Charles River Breeding Laboratory in the United States and provided by Experimental Animal Laboratory of Korea Research Institute of Chemical Technology were used as test animals. The mice subjected to the testing of those end products prepared in Examples 1 to 35 had a body weight of 20 to 25 g; and those used for the testing of the compounds synthesized in Examples 36 to 56 had a weight ranging from 10 to 15 g. They were tested after having been adjusted to the testing environment for a week. Food and water were given freely; and illumination was maintained on a 12-hour cycle.

2) Testing method

Experiments were performed in two ways: that is, the acetic acid induced writhing test and the phenyl-1,4-benzoquinone(PBQ) induced writhing test.

Solutions for the acetic acid induced writhing test were prepared by dissolving one of the end products prepared in Examples 1 to 35 in a saline solution containing 1% by weight of Tween 80 to have a concentration of 5 mg/ml and diluting it serially with the saline solution. The test solutions were administered orally in a dose of 0.3 ml per 30 g of body weight, using the 5 ICR mice for each test. 60 minutes later, 0.9% acetic acid solution was administered intraperitoneally in a dose of 0.1 ml per 30 g of body weight. 3 minutes thereafter, the number of writhings generated during a period of 10 minutes due to the administration of acetic acid was measured. For comparison purpose, initially, saline solution alone was administered orally to the control group. 60 minutes thereafter, 0.9% acetic acid solution was administered intraperitoneally to the control group.

Alternatively, solutions for the PBQ induced writhing test were prepared by dissolving one of the products synthesized in Examples 36 to 56 in a mixture of Tween 80, alcohol and distilled water (1:5:94); and administered orally to the 5 ICR mice for each test in a dose of 0.3 ml per 30 g of body weight. 60 minutes later, 0.2% PBQ solution was administered intraperitoneally in a dose of 0.1 ml per 30 g of body weight of the test animals. 5 minutes thereafter, at the temperature of 40° C., the number of writhings occurred during a period of 5 minutes due to the PBQ solution administered was measured. For comparison, only the mixture of Tween 80, alcohol and distilled water was administered orally to the control group; and, after 60 minutes, the PBQ solution was administered intraperitoneally to the control group in the same manner as mentioned above.

3) Measurement of analgesic effect

The number of writhings suffered by the test group was compared with that of the control group; and the analgesic effect was measured in terms of the percentage of inhibition of writhing(I. W.).

$$I.W. (\%) = \frac{A - B}{A} \times 100$$

A: the number of writhings suffered by the control group,

B: the number of writhings suffered by the test group.

The amount of a test compound which is required in reducing the frequency of writhings to the 50% level of that generated by the control group, i.e., B=0.5 A or I.W.=50%, is designated as $ED_{50}$: therefore, a lower value of $ED_{50}$ represents a higher analgesic effect of the tested compound. These $ED_{50}$ values for the test compounds are shown in the last column of Table 1.

The first column of Table 1 represents the number of each Example; n, $Y_p$ and X expressed in cols. 2 to 4 have the same meanings as defined in Formula(I); the data contained in cols. 5 to 7 describes the respective yield and melting point of the intermediates, i.e., compounds of the formulae(IV), (V) and (VI), employed in preparing the final product of formula(I), whose yield and melting point are stated in the eighth column.

TABLE 1

| Example | n | $Y_p$ | X | Formula (IV) Yield | m.p. | Formula (V) Yield | m.p. | Formula (VI) Yield | m.p. | Formula (I) Yield | m.p. | $ED_{50}$ (mg/Kg) |
|---|---|---|---|---|---|---|---|---|---|---|---|---|
| 1 | 3 | 3,4-Me$_2$ | OMe | 90%, | —*1 | 63%, | 105° C. | 97%, | 105° C. | 94%, | 105° C. | 0.08 |
| 2 | 3 | 3,4-Me$_2$ | H | 90%, | 100° C. | 67%, | 97° C. | 90%, | 105° C. | 94%, | 92° C. | 3.98 |
| 3 | 3 | 3,4-Me$_2$ | F | 88%, | — | 82%, | 97° C. | 93%, | 83° C. | 96%, | 69° C. | 2.95 |
| 4 | 3 | 3,4-Me$_2$ | Cl | 82%, | 109° C. | 90%, | 105° C. | 89%, | 101° C. | 93%, | 71° C. | 4.78 |
| 5 | 3 | H | OMe | — | — | 56%, | 111° C. | 94%, | 89° C. | 95%, | 104° C. | 2.5 |
| 6 | 3 | H | OMe | 96%, | — | 48%, | 94° C. | 86%, | 64° C. | 84%, | 64° C. | 0.20 |
| 7 | 3 | H | OMe | 92%, | 88° C. | 51%, | 104° C. | 96%, | 77° C. | 93%, | 99° C. | 0.79 |
| 8 | 3 | 3-Me | OMe | 91%, | — | 48%, | 116° C. | 98%, | 87° C. | 86%, | 88° C. | 0.07 |
| 9 | 3 | 3-Me | H | 80%, | 88° C. | 66%, | 95° C. | 88%, | 79° C. | 84%, | 88° C. | 26.3 |
| 10 | 3 | 3-Me | F | 88%, | 78° C. | 78%, | 86° C. | 97%, | 55° C. | 98%, | — | 2.3 |
| 11 | 3 | 3-Me | Cl | 96%, | 91° C. | 75%, | 84° C. | 98%, | 58° C. | 97%, | — | 42.6 |
| 12 | 3 | 4-Me | OMe | 95%, | — | 82%, | 139° C. | 95%, | 112° C. | 92%, | 119° C. | 1.73 |
| 13 | 3 | 4-Me | H | 88%, | 140° C. | 87%, | 118° C. | 98%, | 104° C. | 54%, | 91° C. | 7.9 |
| 14 | 3 | 4-Me | F | 92%, | 155° C. | 72%, | 94° C. | 80%, | 79° C. | 76%, | 77° C. | 0.01 |
| 15 | 3 | 4-Me | Cl | 90%, | 133° C. | 91%, | 113° C. | 99%, | 99° C. | 45%, | 78° C. | 4.7 |
| 16 | 3 | 3,5-Me$_2$ | OMe | 95%, | — | 60%, | 109° C. | 77%, | 90° C. | 75%, | 90° C. | 4.6 |
| 17 | 3 | 3,5-Me$_2$ | H | 63%, | 75° C. | 70%, | 114° C. | 80%, | 83° C. | 82%, | 99° C. | 3.16 |
| 18 | 3 | 3,5-Me$_2$ | F | 90%, | 105° C. | 95%, | 91° C. | 94%, | 65° C. | 75%, | 98° C. | 0.02 |
| 19 | 3 | 3,5-Me$_2$ | Cl | 92%, | — | 70%, | 89° C. | 84%, | 68° C. | 94%, | 99° C. | 123 |
| 20 | 2 | 3,5-Me$_2$ | OMe | 78%, | — | 60%, | 130° C. | — | 109° C. | 87%, | 118° C. | 0.77 |
| 21 | 3 | 4-Cl | OMe | 98%, | — | 64%, | 118° C. | 93%, | 95° C. | 92%, | 121° C. | 0.40 |
| 22 | 3 | 4-Cl | H | 90%, | 81° C. | 98%, | 108° C. | 93%, | 97° C. | 95%, | 92° C. | 0.03 |
| 23 | 3 | 4-Cl | F | 75%, | — | 95%, | 74° C. | 82%, | 63° C. | 41%, | 91° C. | 0.07 |
| 24 | 3 | 4-Cl | Cl | 77%, | 136° C. | 83%, | 95° C. | 92%, | 77° C. | 94%, | 77° C. | 0.04 |
| 25 | 3 | 4-F | OMe | — | — | — | — | 80%, | — | — | — | — |
| 26 | 3 | 2,4-Cl$_2$ | OMe | 89%, | — | — | — | — | — | — | — | — |
| 27 | 3 | 3,4-Cl$_2$ | OMe | 84%, | — | 68%, | 102° C. | 80%, | 108° C. | 75%, | 114° C. | 0.66 |
| 28 | 3 | 3,4-(CH$_2$O$_2$)$_2$ | OMe | 84%, | — | 67%, | 125° C. | 94%, | 112° C. | 92%, | 106° C. | 0.8 |
| 29 | 3 | 3-CF$_3$ | OMe | 98%, | — | 62%, | 104° C. | 95%, | 92° C. | 91%, | 90° C. | 1.54 |
| 30 | 3 | 3-OMe | OMe | — | — | — | — | — | — | — | — | 1.25 |
| 31 | 3 | 3-OCH$_2$Ph | OMe | 65%, | — | — | — | — | — | — | — | 28.8 |
| 32 | 3 | 3,4-(OMe)$_2$ | OMe | 93%, | — | 61%, | 126° C. | 93%, | 86° C. | 91%, | 126° C. | — |
| 33 | 4 | 3-Me | OMe | 91%, | — | 65%, | 92° C. | 98%, | 63° C. | 90%, | 107° C. | 1.54 |
| 34 | 4 | 3-Me | H | 84%, | 85° C. | 84%, | 92° C. | 81%, | 83° C. | 89%, | 113° C. | 3.3 |
| 35 | 4 | 3,4-Me$_2$ | F | — | — | — | — | — | — | — | — | 1.44 |

TABLE 1-continued

| Example | n | $Y_p$ | X | Formula (IV) Yield | m.p. | Formula (V) Yield | m.p. | Formula (VI) Yield | m.p. | Formula (I) Yield | m.p. | $ED_{50}$ (mg/Kg) |
|---|---|---|---|---|---|---|---|---|---|---|---|---|
| 36 | 3 | 3,4-Me$_2$ | OH | 87%, | 66° C. | 85%, | 75° C. | 84%, | 106° C. | 87%, | 147° C. | 0.49 |
| 37 | 3 | 3-Me | OH | 89%, | — | 87%, | 93° C. | 97%, | 96° C. | 92%, | dec. | — |
| 38 | 3 | 4-OMe | OH | 66%, | — | 85%, | 118° C. | 57%, | 112° C. | 61%, | 125° C. | — |
| 39 | 3 | 3,4-(CH$_2$O$_2$)$_2$ | OH | 47%, | — | — | — | — | 115° C. | — | — | — |
| 40 | 3 | 3,4-Me$_2$ | NH$_2$ | 90%, | 103° C. | 94%, | 93° C. | 97%, | 89° C. | 94%, | 98° C. | 22.7 |
| 41 | 2 | H | NH$_2$ | 86%, | 85° C. | 85%, | 121° C. | 90%, | 78° C. | 99%, | 243° C. | — |
| 42 | 3 | H | NH$_2$ | 90%, | — | — | 74° C. | 98%, | 70° C. | 93%, | 96° C. | 75.9 |
| 43 | 4 | H | NH$_2$ | 97%, | 85° C. | 83%, | 96° C. | 98%, | 95° C. | 99%, | 245° C. | — |
| 44 | 5 | H | NH$_2$ | 77%, | 91° C. | 87%, | 93° C. | 99%, | 80° C. | 94%, | 245° C. | 101 |
| 45 | 3 | 3-Me | NH$_2$ | — | 97° C. | 88%, | 58° C. | 94%, | 50° C. | 97%, | 74° C. | 22.1 |
| 46 | 3 | 4-Cl | NH$_2$ | 82%, | 90° C. | 81%, | 58° C. | 99%, | 115° C. | 99%, | 249° C. | 77.6 |
| 47 | 3 | 4-F | NH$_2$ | 85%, | 132° C. | 84%, | 78° C. | 99%, | 101° C. | 99%, | 238° C. | 37.8 |
| 48 | 3 | 3,4-Cl$_2$ | NH$_2$ | 94%, | 115° C. | 99%, | 55° C. | 99%, | 89° C. | 99%, | 240° C. | 7.18 |
| 49 | 3 | 3-CF$_3$ | NH$_2$ | 83%, | 94° C. | 87%, | 112° C. | 94%, | 75° C. | 93%, | 190° C. | — |
| 50 | 3 | 3,4-Me$_2$ | NO$_2$ | — | — | — | — | — | — | 82%, | 98° C. | 22.5 |
| 51 | 2 | H | NO$_2$ | — | — | — | — | — | — | 82%, | 98° C. | 22.5 |
| 52 | 4 | H | NO$_2$ | — | — | — | — | — | — | 65%, | 104° C. | — |
| 53 | 5 | H | NO$_2$ | — | — | — | — | — | — | 54%, | 98° C. | — |
| 54 | 3 | 4-F | NO$_2$ | — | — | — | — | — | — | — | — | — |
| 55 | 3 | 3,4-Cl$_2$ | NO$_2$ | — | — | — | — | — | — | 40%, | 83° C. | — |
| 56 | 3 | 3-CF$_3$ | NO$_2$ | — | — | — | — | — | — | 62%, | 60° C. | — |
| NE-21610*[2] | | | | | | | | | | | | >300 |

*[1] "—" signs represent data not available.
*[2] N-{4-(2-aminoethoxy)-3-methoxybenzyl)}oleamide, The Procter & Gamble Company (covered in U.S. Pat. No. 5,045,565)

2. Behavior Analysis

In order to monitor a harmful side-effect or toxicity of the compounds having the formula(I), various behavioral changes in the test animals were observed. After the test and the control solutions were administered to the animals, such symptoms as sedation, ptosis, dyspnoea, vasolidation, convulsion, salivation and urination were observed and the level of such changes was represented by a numbering system: that is, the normal value of the last three behaviors(i.e., urination, convulsion and salivation) is 0; and that of the others(i.e., sedation, ptosis, dyspnoea and vasolidation) is 4. The higher the number is, the greater the side effects are. The test results for some of the compounds are shown in Table 2.

TABLE 2

| Compounds | | Behavior | | | | | | |
|---|---|---|---|---|---|---|---|---|
| Example | dose | Sedation | Ptosis | Dyspnoea | Vasolidation | Convulsion | Salivation | Urination |
| 36 | 2.0 mg/Kg | 7 | 6 | 5 | 4 | 0 | 0 | 0 |
|  | 0.6 mg/Kg | 5 | 4 | 4 | 4 | 0 | 0 | 0 |
|  | 0.2 mg/Kg | 4 | 4 | 4 | 4 | 0 | 0 | 0 |
| 40 | 60 mg/Kg | 6 | 6 | 4 | 4 | 0 | 0 | 0 |
|  | 20 mg/Kg | 4 | 5 | 4 | 4 | 0 | 0 | 0 |
|  | 6.7 mg/Kg | 4 | 4 | 4 | 4 | 0 | 0 | 0 |
| 42 | 200 mg/Kg | 5 | 7 | 5 | 4 | 0 | 0 | 0 |
|  | 100 mg/Kg | 4 | 4 | 4 | 4 | 0 | 0 | 0 |
|  | 50 mg/Kg | 4 | 4 | 4 | 4 | 0 | 0 | 0 |
| 44 | 200 mg/Kg | 6 | 6 | 4 | 4 | 0 | 0 | 0 |
|  | 66.7 mg/Kg | 4 | 4 | 4 | 4 | 0 | 0 | 0 |
|  | 22.2 mg/Kg | 4 | 4 | 4 | 4 | 0 | 0 | 0 |
| 45 | 60 mg/Kg | 6 | 7 | 7 | 4 | 0 | 0 | 0 |
|  | 20 mg/Kg | 4 | 5 | 4 | 4 | 0 | 0 | 0 |
|  | 6.7 mg/Kg | 4 | 4 | 4 | 4 | 0 | 0 | 0 |
| 46 | 50 mg/Kg | 4 | 4 | 4 | 4 | 0 | 0 | 0 |
|  | 25 mg/Kg | 4 | 4 | 4 | 4 | 0 | 0 | 0 |
|  | 10 mg/Kg | 4 | 4 | 4 | 4 | 0 | 0 | 0 |
| 47 | 50 mg/Kg | 4 | 4 | 4 | 4 | 0 | 0 | 0 |
|  | 25 mg/Kg | 4 | 4 | 4 | 4 | 0 | 0 | 0 |
|  | 10 mg/Kg | 4 | 4 | 4 | 4 | 0 | 0 | 0 |
| 48 | 100 mg/Kg | 6 | 5 | 5 | 4 | 0 | 0 | 0 |
|  | 50 mg/Kg | 5 | 4 | 4 | 4 | 0 | 0 | 0 |
|  | 25 mg/Kg | 4 | 4 | 4 | 4 | 0 | 0 | 0 |
| 50 | 100 mg/Kg | 7 | 7 | 4 | 4 | 0 | 0 | 0 |
|  | 33.3 mg/Kg | 4 | 4 | 4 | 4 | 0 | 0 | 0 |
|  | 11.1 mg/Kg | 4 | 4 | 4 | 4 | 0 | 0 | 0 |
| NE-21610 | 100 mg/Kg | 7 | 7 | 6 | 4 | 2 | 0 | 0 |
|  | 50 mg/Kg | 5 | 5 | 4 | 4 | 0 | 0 | 0 |
|  | 25 mg/Kg | 4 | 4 | 4 | 4 | 0 | 0 | 0 |
|  | 10 mg/Kg | 4 | 4 | 4 | 4 | 0 | 0 | 0 |

3. Randal-Selitto Test

Randall-Selitto Test was carried out by following the method described in Arch. Int. Pharmacodyn. 11, 409(1957).

Male albino rats (120–170 g) of the Charles River Sprague-Dawley strain were used. Inflammation was produced by the injection of 0.1 ml of a 20% suspension of Brewer's yeast into the plantar surface of the rat's hind foot. Thresholds were determined using a modified apparatus described in Winter and Flataker (J. Pharm. Exp. Ther. 148, 373(1965)).

The pain threshold was measured as the pressure in mmHg required to induce the desired response (a sharp audible squeak and/or struggle) when the pressure was applied to the foot. Air pressure from an air line was admitted through a needle valve to a 20 ml glass syringe and to a pressure gauge which was connected by a T-tube. The syringe was mounted with the plunger downward to which was connected a short bullet-shaped Teflon peg. The pressure was applied to the foot of the rat at the rate of 10 mmHg per second. Drug was given 2 hours after the yeast injection. Two hours after the drug administration, threshold response was determined. The results were compared with the results obtained from the yeast-treated, saline control group, as shown in Table 3.

The analgesic activity was determined in terms of the percentage of inhibition of response:

$$\text{Inhibition (\%)} = \frac{\text{Threshold of the treated group} - \text{Threshold of the control group}}{\text{Threshold of the control group}} \times 100$$

The compound of Example 1, administered two hours after yeast injection and one hour before the test at a dose of 5 mg/kg perorally, caused an inhibition of yeast induced hyperalgesia.

TABLE 3

| Compound | Dose (mg/Kg) | Number of rats | Inhibition (%) |
|---|---|---|---|
| Aspirin[1] | 100 (s. c.) | 10 | 80.1 |
| Ketoprofen[2] | 10 (p. o.) | 8 | 62.1 |
| Morphine[3] | 3 (s. c.) | 8 | 391.7 |
| Example 1 | 5 (p. o.) | 5 | 247.4 |
| Example 1-HCl | 1.5 (s. c.) | 8 | 248.3 |

[1]Bayer, U.S. Pat. No. 3,235,583
[2]Rhone-Poulenc, U.S. Pat. No. 3,641,127
[3]U.S. Pat. No. 2,740,787

4. Tail-flick Test

The tail flick assay of D'Amour and Smith (J. Pharm. Exp. Ther. 72, 74(1941)) was modified for use with mice. Radiant heat was applied using a beam of high-intensity light focused on a tail spot. The response time, defined as the interval between the onset of the stimulus and the tail flick, was measured electronically (to the nearest 0.1 second). The beam intensity was set at a level giving a mean control reaction time of $3.8 \pm 0.4$ seconds. Animals that did not flick their tails within 15 seconds were removed and assigned a 15-second response latency.

The inhibition rates (analgesic effects) of the compound of Example 1 and standard compounds are shown in Table 4. The percentage of inhibition was determined by the following equation:

$$\text{Inhibition (\%)} = \frac{\text{Reaction time of the treated group} - \text{Reaction time of the control group}}{\text{Reaction time of the control group}} \times 100$$

Morphine used as reference was active in this test; but nonsteroidal anti-inflammatory drugs were ineffective. The results show that the compound of Example 1 is more effective than morphine and suggest that the Example 1 compound behaves as a central analgesic.

TABLE 4

| Compound | Dose (mg/Kg) | Inhibition (%) |
|---|---|---|
| Aspirin (p. o.) | 100 | 0 |
| Piroxicam (p. o.)[1] | 100 | 0 |
| Capsaicin | 25 | 90 |
| Morphine-HCl (s. c.) | 2.0 | 57 |
|  | 5.0 | 100 |
| NE-21610 (p. o.)[2] | 200 | 50 |
| Example 1 (s. c.) | 0.5 | 50 |
|  | 1.0 | 70 |
| Example 1 (p. o.) | 1.25 | 10 |
|  | 2.5 | 60 |
|  | 5.0 | 80 |
|  | 7.5 | 90 |
| Example 1-l-tartarate (p. o.) | 1.25 | 50 |
|  | 2.5 | 90 |
| Example 40 (p. o.) | 100 | 50 |
| Example 40-HCl (p. o.) | 50 | 67 |
| Example 42 (p. o.) | 100 | 40 |
| Example 50 (p. o.) | 200 | 38 |

[1]Pfizer, U.S. Pat. No. 3,591,584
[2]P & G, U.S. Pat. No. 5,045,565

5. Hot-plate Test

Mice were placed on an aluminum plate maintained at $55° \pm 0.5°$ C. by a thermo-regulator (Harvard). A glass cylinder, 15 cm in height and 15 cm in diameter, served to confine the mice to the heated plate. Blowing of the fore paws was used as the end-point for determination of response latency (measured to the nearest 0.1 second). Animals which failed to react within 30 seconds were removed and assigned a 30-second response latency.

The inhibition rates of the compound of Example 1 (p. o.) and morphine (s. c.) in the hot plate test were determined by the same equation as used in Tail-flick Test, which are shown in Table 5. This result shows that the compound of Example 1 (p. o.) is as effective as morphine (s. c.) and also suggests that the compound of Example 1 behaves as a central analgesic.

TABLE 5

| Compound | Dose (mg/Kg) | Inhibition (%) |
|---|---|---|
| Morphine-HCl (s. c.) | 2.0 | 27.5 |
|  | 5.0 | 49.0 |
|  | 10.0 | 98.0 |
| Example 1 (p. o.) | 2.5 | 28.6 |
|  | 5.0 | 48.9 |
|  | 10.0 | 97.0 |

6. Tail-pinch test in rats with hyperalgesia induced by Freund's adjuvant

Rats (Sprague-Dawley) weighing 120 g to 170 g were used. Desiccated *Mycobacterium butyricum* (Difco Laboratories, Detroit, Mich.) was ground in a mortar, suspended in liquid paraffin, sterilized in an autoclave, and injected (0.5 mg in 0.1 ml, s.c.) in the distal region of the tail through a 1-inch 21-gauge needle.

Animals so treated exhibited hypersensitivity to the pressure placed on the tail within a few hours of the injection and were used for analgesic testing 18 to 24 hours after injection. The hypersensitivity of the tail was examined as follows: the animal was held comfortably in one hand and gentle pressure was applied with the fingers of the opposite hand to the injected area. This gentle squeeze or "tail pinch" elicited a "squeak" from the animal. Five such stimuli were given at 4-second intervals. If the animal emitted no more than one squeak in five trials, it was recorded as having analgesia and given a rating of 1. If there was more than one squeak, the rating was given the value of 0.

The analgesic activity was determined by the following equation:

$$\text{Analgesic activity} = \frac{\text{Total rating}}{\text{Tested animal number}} \times 100$$

The compound of Example 1, administered two hours before tail-pinch testing perorally, caused a dose related inhibition of adjuvant induced hyperalgesia, as shown in Table 6.

TABLE 6

| Compound | Dose (mg/Kg) | Number of rats | Analgesic activity (%) |
|---|---|---|---|
| Naproxen[1] | 5 | 7 | 28.6 |
| Example 1 | 5 | 7 | 45.9 |
|  | 10 | 6 | 66.7 |

[1]Syntex, U.S. Pat. No. 3,637,767

7. Anti-inflammatory Test

Rats(Sprague-Dawley, female) weighing 100 to 120 g were used. Twenty minutes after the test drug was administered(s. c.), carrageenin was injected(0.1 ml of 1% solution, s. c.) in the plantar surface of the right hand paw. The volume of the edema was measured with a volumeter(Rehma Volumeter 2060) 3 hours later.

The percentage of inhibition was determined by the following equation:

$$\text{Inhibition (\%)} = \frac{\text{Volume of the carrageenin treated foot} - \text{Volume of the control foot}}{\text{Volume of the control foot}} \times 100$$

The amount of a test compound which is required in obtaining 50% inhibition is designated as $ED_{50}$.

The inhibitory effects of Example 1 and 8 were comparable to that of Ketoprofen, but significantly superior to that of Aspirin or Naproxen, as shown in table 7.

TABLE 7

| Compound | $ED_{50}$ (mg/Kg) | Compound | $ED_{50}$ (mg/Kg) |
|---|---|---|---|
| Ketoprofen | 7.2 | Naproxen | 43.0 |
| Aspirin | 109 | Example 8 | 16.9 |
| Example 1 | 4.0 |  |  |

8. Local Anti-inflammatory Test

Rats(Sprague-Dawley, female) weighing 100 to 120 g were used. 20 minutes after the test drug was administered transdermally (another application 7 hours later for double dose experiment), carrageenin was injected(0.1 ml of 1% solution, s. c.) into the plantar surface of the right hind paw. The volume of the edema was measured with a volumeter either 1 hour later for single dose experiment or 24 hours later for double dose experiment; and the percentage of inhibition was measured by the same equation as used in Anti-inflammatory Test.

The inhibitory effect of the compound of Example 1 was slightly better than that of Naproxen, as shown in Table 8.

TABLE 8

| Compound | Single Dose (1 hr) | Double Dose (24 hr) |
|---|---|---|
| Narproxen | 54% | 25% |
| Example 1 | 66% | 32% |

TEST OF TOXICITY

In addition, the acute toxicity test for the compound of Example 1 was carried out at $LD_{50}$ by per os administering the test compound in varied amounts in a stepwise manner into 5 ICR male mice and 5 ICR female mice(5 weeks old), which were observed for 14 days. The $LD_{50}$ values of the compound of Example 1 are 224 mg/Kg(male mice) and 364 mg/Kg(female mice).

We claim:

1. A novel phenylacetamide compound and pharmaceutically acceptable salts thereof, of formula(I)

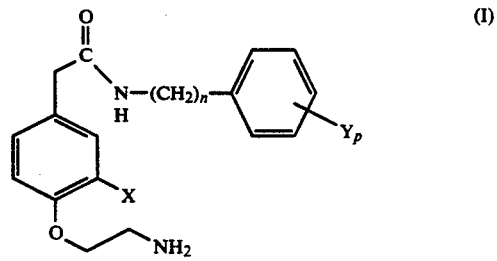

wherein:
X is a hydrogen, halogen, hydroxy, nitro, amino, $R^1$, $NR^1R^2$, $NHR^1$ or $OR^1$ wherein $R^1$ and $R^2$ are an optionally substituted $C_{1-8}$ alkyl, cycloalkyl or benzyl group, respectively;

Y, which may be the same or different when p is greater than 1, is a hydrogen, halogen, methylenedioxy, hydroxy, trifluoromethyl, $R^3$ or $OR^3$ wherein $R^3$ is an optionally substituted $C_{1-8}$ alkyl or benzyl group;

n is an integer from 1 to 6; and
p is an integer from 1 to 5.

2. The compound of claim 1 wherein X is a hydrogen, halogen, hydroxy, nitro, amino or $OR^1$; Y, which may be the same or different when p is greater than 1, is a hydrogen, halogen, trifluoromethyl or $R^3$; n is an integer from 2 to 5; and p is an integer from 1 to 3.

3. The compound of claim 1 wherein X is a halogen, hydroxy, nitro, amino or $OR^1$; Y, which may be the same or different when p is 2, is a hydrogen, halogen, trifluoromethyl or $R^3$; n is 3 or 4; and p is 1 or 2, wherein $R^1$ and $R^3$ are an optionally substituted $C_{1-5}$ alkyl group, respectively.

4. The compound of claim 3 wherein $R^1$ and $R^3$ are an optionally substituted $C_{1-3}$ alkyl group, respectively.

5. The compound of claim 4 wherein X is a methoxy group.

6. The compound of claim 4 wherein X is a hydroxy group.

7. The compound of claim 4 wherein X is a nitro or amino group.

8. The compound of claim 1 which is N-{(3,4-Dimethylphenyl)propyl}-4-(2-aminoethoxy)-3-methoxyphenylacetamide.

9. The compound of claim 1 which is N-{(3,4-Dimethylphenyl)propyl}-4-(2-aminoethoxy)-3-hydroxyphenylacetamide.

10. The compound of claim 1 which is N-{(3,4-Dimethylphenyl)propyl}-4-(2-aminoethoxy)-3-aminophenylacetamide.

11. The compound of claim 1 which is N-{(3-Methylphenyl)propyl}-4-(2-aminoethoxy)-3-methoxyphenylacetamide.

12. The compound of claim 1 which is N-{(3-Methylphenyl)propyl}-4-(2-aminoethoxy)-3-hydroxyphenylacetamide.

13. The compound of claim 1 which is N-{(3-Methylphenyl)propyl}-4-(2-aminoethoxy)3-aminophenylacetamide.

14. A pharmaceutically acceptable salt of claim 1 wherein the salts are selected from the group consisting of salts obtained by reacting a compound of formula I with an inorganic acid selected from the group consisting of hydrochloric acid, hydrogen bromide, sulfuric acid, sodium hydrogen sulfate and carbonic acid; and with an organic acid selected from the group consisting of formic, acetic, oxalic, benzoic, citric, tartaric, gluconic, gentisic, fumaric and lactobionic acid.

15. A pharmaceutical composition comprising, as active ingredient, a compound of formula (I) as defined in claim 1 or a pharmaceutically acceptable salt thereof, in a pharmaceutically acceptable carrier.

* * * * *